US005585732A

United States Patent [19]
Steele et al.

[11] Patent Number: 5,585,732
[45] Date of Patent: Dec. 17, 1996

[54] DETECTOR FOR HETEROGENEOUS MATERIALS

[75] Inventors: Philip H. Steele; Lalit Kumar, both of Starkville, Miss.

[73] Assignee: Mississippi State University, Mississippi State, Miss.

[21] Appl. No.: 473,945

[22] Filed: Jun. 7, 1995

[51] Int. Cl.$^6$ .................................................. G01R 27/26
[52] U.S. Cl. ........................ 324/663; 324/690; 73/304 C
[58] Field of Search .................... 324/664, 663, 324/686, 687, 690; 73/304 C, 866.5; 364/550; 340/602, 618, 604

[56] References Cited

U.S. PATENT DOCUMENTS

| | | |
|---|---|---|
| 2,544,673 | 3/1951 | Haber . |
| 3,185,924 | 5/1965 | Locher . |
| 3,354,388 | 11/1967 | Perry . |
| 3,423,991 | 1/1969 | Collins . |
| 3,430,357 | 3/1969 | Perry . |
| 3,477,021 | 11/1969 | Dosch et al. . |
| 3,549,986 | 12/1970 | Prine . |
| 3,694,742 | 9/1972 | Bergmanis et al. . |
| 3,805,156 | 4/1974 | Norton et al. . |
| 3,810,005 | 5/1974 | Bennion et al. . |
| 4,123,702 | 10/1978 | Kinanen et al. . |
| 4,201,093 | 5/1980 | Logan . |
| 4,208,625 | 6/1980 | Piso . |
| 4,259,633 | 3/1981 | Rosenau . |
| 4,500,835 | 2/1985 | Heikkila . |
| 4,616,425 | 10/1986 | Burns . |
| 4,922,181 | 5/1990 | Pullan . |
| 4,941,357 | 7/1990 | Schajer . |
| 4,972,154 | 11/1990 | Bechtel et al. . |
| 5,357,112 | 10/1995 | Steele et al. . |
| 5,394,097 | 2/1995 | Bechtel et al. ........................ 324/687 |
| 5,486,815 | 1/1996 | Wagner ................................. 340/602 |

FOREIGN PATENT DOCUMENTS

| | | |
|---|---|---|
| 53365 | 12/1977 | Finland . |
| 1489554 | 10/1977 | United Kingdom . |

Primary Examiner—Vinh P. Nguyen
Attorney, Agent, or Firm—Oblon, Spivak, McClelland, Maier & Neustadt, P.C.

[57] ABSTRACT

A system for the detection of knots and voids in wood or lumber employs opposed arrays of capacitor plates. The presence of knots and/or voids is detected based on changes in the dielectrical response produced in the electrical fields defined by the opposed capacitor plate arrays. A software system delineates specific knot and void defects determined. Wood or lumber strength can further be estimated by comparing a sensed dielectric value in a clear portion of the lumber or wood with an established dielectric response value for wood of known density. Employing an appropriate correlation factor the relative wood density, coupled with knot/void location and size, permits an estimate of over all wood strength.

12 Claims, 4 Drawing Sheets

DETECTOR FOR HETEROGENEOUS MATERIALS

BACKGROUND OF THE INVENTION

1. Field of the Invention

The invention disclosed and claimed in this application pertains to a method for (1) determining the presence and location of knots and voids in wood and/or (2) for estimating wood strength. Throughout this disclosure reference will be made to wood scanning. The term wood means any solid wood product containing knots and/or voids such as lumber, veneer, etc. Specifically, the invention employs opposed multiple flat-electrode capacitors to create an electrical field through which the wood is passed. The dielectric response (capacitance and resistance) properties of knots, voids, and clear wood differ. When measured across the wood thickness the dielectric response of knots is higher and the dielectric response of voids is lower than for clear wood. Analog voltage values indicate the dielectric response properties of the wood thickness between opposing capacitor electrodes. This analog information is input to a data acquisition device and computer hardware converts the analog signals to digital values. The digital values are stored in a two-dimensional array that describes the wood dielectric response. The array is analyzed to determine which values indicate the presence of knots and which values indicate the presence of voids in the piece of wood that passed through the electric field. The computer locates and delineates the detected array values corresponding to knots and the detected values corresponding to voids with rectangles. This information may be used to evaluate wood quality, to control saws for lumber cutup, veneer sorting, or to control other special treatment apparatus and operations, etc. The invention may be used alone if only knots and voids are to be detected. On the other hand, the invention may be used with other defect detection devices such as CCD cameras, laser detectors, etc. as a component of a larger system designed to detect defect types in addition to knots and voids.

2. Background of the Prior Art (1) Knot and Void Detection

A defect detection device is disclosed in Pullan, U.S. Pat. No. 4,922,181. The Pullan patent discloses a device for detecting defects in blister packs and laminated boards. The device disclosed by Pullan employs a single signal generating capacitor electrode and multiple receiving electrodes. By contrast, the detector of the present invention has signal generating capacitor plates of the same size as its signal receiving capacitor plates. In addition, the device disclosed by Pullan employs an operator as a component of the system to detect defects. The operator visually monitors a video screen on which the image of the dielectric constant information is displayed. By contrast, the present invention employs a computer system with specialized software to detect differences in the dielectric field that indicate the presence of knots and voids.

The device disclosed in the Pullan patent is also suited only for the detection of defects in materials for which the expected dielectric is known. Wood is a heterogeneous material with potentially large differences in moisture content and density between respective pieces such as boards, sheets of veneer, etc. Moisture content and density strongly influence the dielectric properties of individual pieces of wood.

Because the dielectric response of wood differs considerably between pieces due to density and moisture content differences, it is best, for the purpose of knot and void detection, not to assume an expected dielectric response for either clear wood or defects. The recognition of knots and voids by dielectrics in wood is best accomplished by accounting for the large between-piece differences in dielectric response. A device capable of sensing knots and voids in wood should possess a means for between-board recalibration so that the clear wood, knot wood and voids contained in each piece of wood can be recognized as such. The device disclosed in the Pullan patent lacks this recalibration function. The computer software incorporated in the system of the present invention provides the required recalibration capability for each piece of wood regardless of the degree of differences in moisture content and density between boards, sheets of veneer, etc.

Bechtel et al., U.S. Pat. No. 4,972,154, discloses a slope-of-grain detector capable of detecting knots and voids in wood. This device applies an electrical field to one surface of the wood and differences in the dielectric response allow determination of the grain angle. The electric field encounters less resistance along the grain compared to the across-the-grain travel. To determine slope-of-grain, the electrical field is sampled by a sensor composed of receiving electrodes arranged in a circular configuration around a sending electrode. By sampling at eight angles around a central receiving capacitor the actual slope-of-grain is determined based on the angle from which the highest dielectric response value is received.

The slope-of-grain device described in the Bechtel et al. patent was itself an improvement of a device disclosed in Norton et al., U.S. Pat No. 3,805,156, which corresponds to Canadian Patent No. 943,187. The device disclosed in the Norton et al. patent measures slope-of-grain using a pair of electrodes comprising a capacitor that mechanically rotates in a circular direction. As with the device disclosed in the Bechtel et al. patent, the circular design determines slope-of-grain based on the highest dielectric response sampled on the 360 degrees arc of travel.

The circular design of the devices of both the Bechtel et al. and Norton et al. patents accomplish the recalibration process required for a heterogeneous material, but in an entirely different way than does the present invention. The circular sampling of the dielectric response by the devices disclosed in the Bechtel et al. and the Norton et al. patents is done at high speed (8 kHz for the Bechtel et al. and 1200 rpm for the Norton et al.). This high speed and the fact that it is the computed difference in the dielectric response for each capacitor revolution that is used to determine grain angle results in what is essentially a recalibration of the sensor for each revolution. It matters little whether moisture content or density change even within a piece of wood if it is the highest dielectric response value per revolution that determines the wood grain angle.

Some previous non-contact devices to detect knots and voids across wood thickness have utilized microwaves (Innotec Ltd., British Patent Specification No 1,489,554; Heikkila and Osakeyhtio; Finnish Patent Publication No. 53,365; Prine, U.S. Pat. No. 3,549,986; Kinanen and Drucker, U.S. Pat. No. 4,123,702; Heikkila and Osakeyhtio, U.S. Pat. No. 4,500,835). Another device (Flatman et al., International Patent WO90/11488) employs x-rays to determine the across-wood-thickness density for detection of knots and voids. The present invention differs from those devices in the use of capacitor plates to generate an electrical field in the radio frequency range rather than in the microwave or x-ray spectrum. The advantage of the radio frequency range signal is that the flat-electrode capacitors required for signal generation and receiving are very low in cost. Equipment for generation of microwaves requires antennae that are much more costly than capacitors. Likewise, generation of radiation beams for through-wood knot and void detection requires a device with relatively high capital cost.

(2) Estimation of Wood Strength

A method of estimating wood strength is disclosed in Shajer, U.S. Pat. No. 4,941,357. That patent discloses a process comprising passing a beam(s) from a radiation source through the lumber thickness to determine the wood density profile across the lumber width. Multiple density profiles across the lumber width may be obtained along the lumber length depending on the sampling frequency and the lumber length, as the piece of lumber travels through the beam(s). Differential absorption of the radiation identifies both knots and the density of clear wood between and around the knots. Comparison of sensed clear wood density to a known base density allows estimation of the strength of the clear wood portion. The known strength of the base density and the correlated strength increase of wood as the radiation beam is attenuated allows the estimation of the strength of the sensed wood density. Sensed knot density allows differentiation of knots. Knot size and location are employed to predict the structural influence on wood strength. The combined information on strength of clear wood and knot influence on this strength allows an estimation of wood strength.

The present invention can also be used to determine wood strength by employing the electric field generated between the electrodes comprising the capacitor.

In this configuration, knot defects can be detected with the array technique previously described. However, comparison of the dielectric values of the clear wood to a base value for the purpose of estimating the density and thereby inferring the clear wood strength cannot be achieved by comparison between array values. The array dielectric response values representing clear wood must be compared to a known dielectric response base value. As previously discussed, higher moisture content values in wood of the same density will result in higher sensed dielectric response values. Therefore, for the present invention to be employed in the wood strength estimation mode an estimate of wood moisture content must be obtained. The influence of the moisture content on density must also be known to allow a correction factor to be applied to obtain an accurate estimate of wood density.

The problem with wood moisture content is not unique to the present invention. The same problem exists with the radiation method described by Shajer. Shajer, however, did not discuss this problem or a solution to this problem in his patent.

There are several non-contact in-line moisture content sensing devices available, for example, the Wagner 683 In-Line Moisture Detector. These in-line moisture content sensing devices are accurate for moisture contents between 6 and 25 percent which is an adequate range to determine moisture content in kiln-dried softwood and hardwood lumber. Veneer moisture content may be lower than 6 percent. Thus, in the case of veneer, the problem of corrections for a wide range of moisture contents does not normally exist because the range is usually between zero and 6 percent. The in-line moisture meter can be placed in-line just before or after the scanning capacitors of the present invention to determine the moisture content along each piece of wood's length. Based on the sensed moisture content, the density values of wood that were computed without regard to moisture content can be corrected.

SUMMARY OF THE INVENTION (1) Knot and Void Detection

The present invention is a system in which capacitor plates generate an electrical field in the radio frequency range through the thickness of a piece of wood. The capacitor plates do not touch the wood surface but are at a distance from it. The opposed capacitor plates are of identical size and shape. Knot and void defects are detected based on the change in the dielectric response that they produce in the electric field. The capacitor plates may be used singly, in linear, or diagonal arrays or in any other arrangement that will allow an adequate sampling to provide a description of the board as a two-dimensional array of across-wood-thickness dielectric values. Capacitor electrodes may be of any size but resolution is improved as plate size is reduced. The capacitor electrodes may be of any shape but a square or circular shape is preferred.

The sensed dielectric response values are input to a computer via a data acquisition system. Analog signals are converted to digital values by an analog-to-digital converter. Special computer software creates a two-dimensional array of digital dielectric values describing the dielectric properties of each scanned board. Other special software analyzes the dielectric response array values and determines the dielectric response value of the clear wood in each piece at its current moisture content. Identification of the dielectric response of clear wood in each piece allows a search for knot or void areas which have a dielectric response different from clear wood. Following identification of knots and voids in the array, the software delineates knot and void defects with rectangles. While the rectangles may be graphically represented on a computer monitor for development or testing purposes, this will not be done in a production situation. In a production situation the rectangular information will be stored as data in the computer controlling the scanning system. The rectangular data will be employed to indicate how close to the knots or voids saws may pass in order to cut the defects from the wood, where veneer patching may need to be performed, etc.

(2) Estimation of Wood Strength

In the configuration of the present invention for estimating lumber strength, the array method is also employed to determine size and location of knots and voids that will influence wood strength. In addition, the density of clear wood is estimated by comparing the sensed clear wood dielectric values to a base dielectric response value for wood of known density. An appropriate correction factor must then be employed to estimate the unknown clear wood density from the base value. The relationship of clear wood dielectric response value to wood density must be known to allow the correction factor to be applied to the base value. The combined information on estimated clear wood density and knot location and size allows an estimate of wood strength.

Figure 1:
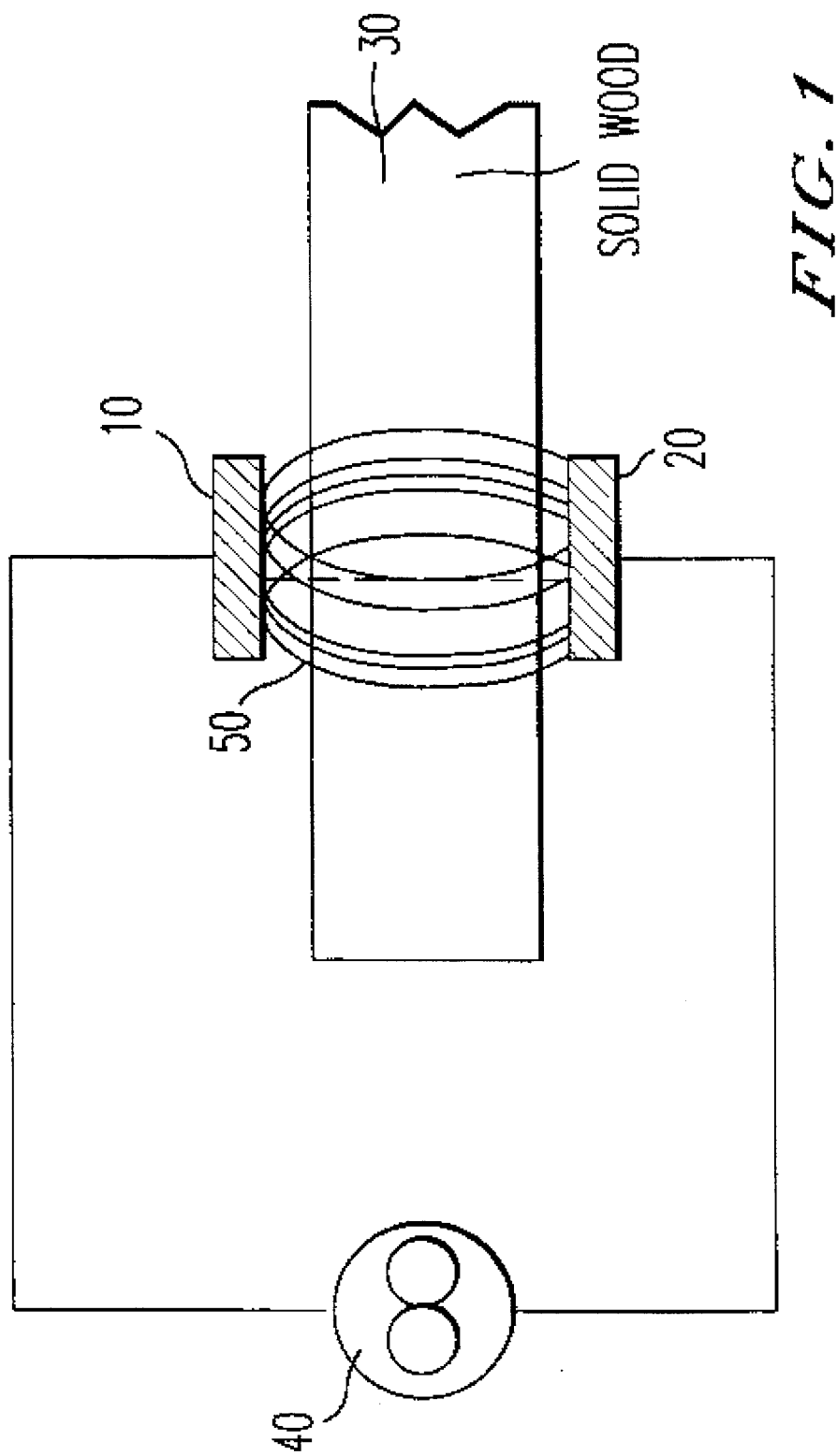
FIG. 1 illustrates a pair of electrodes on opposite sides of a piece of lumber or veneer and with the electrodes connected to an oscillator for generating an alternating voltage in the radio frequency range.

DESCRIPTION OF THE PREFERRED EMBODIMENTS (1) Detection of Knots and Voids

The present disclosure describes a new device that employs dielectric response sensors (FIG. 1) to detect knots and voids in pieces of lumber. Each sensor consists of two electrodes 10,20 connected to an oscillator 40. One capacitor electrode 10 is placed on one side of the scanned material 30. The second capacitor electrode 20 is positioned opposite the first electrode 10 on the opposite side of the scanned material 30. The capacitor electrode 10, on one side may usually be the same size and shape as on the opposite side, but this is not a requirement. An alternating current signal is supplied by an RF generator. The signal is amplified by an RF amplifier 35 and is then input to the driven capacitor electrode 10. The alternating current voltage is supplied in the range of 10–40 volts RMS. The signal applied to the capacitor electrodes produces an electric field 50 that passes through the scanned material and is received by the top capacitor electrode 20. The resistance to the passage of the electric field 50 through the scanned material 30 varies, depending on the dielectric response properties of the material.

The sensor shown in FIG. 1 is a capacitance bridge incorporating the scanned material as part of the bridge. In the absence of material 30 between the capacitor electrodes 10,20, the bridge is completed by the presence of air between the electrodes 10,20 and the dielectric response of the air between the electrodes 10,20 is measured. When wood material 30 is present between the capacitor electrodes 10,20, the bridge measures the dielectric response of the material 30 in the electric field 50.

Figure 2:
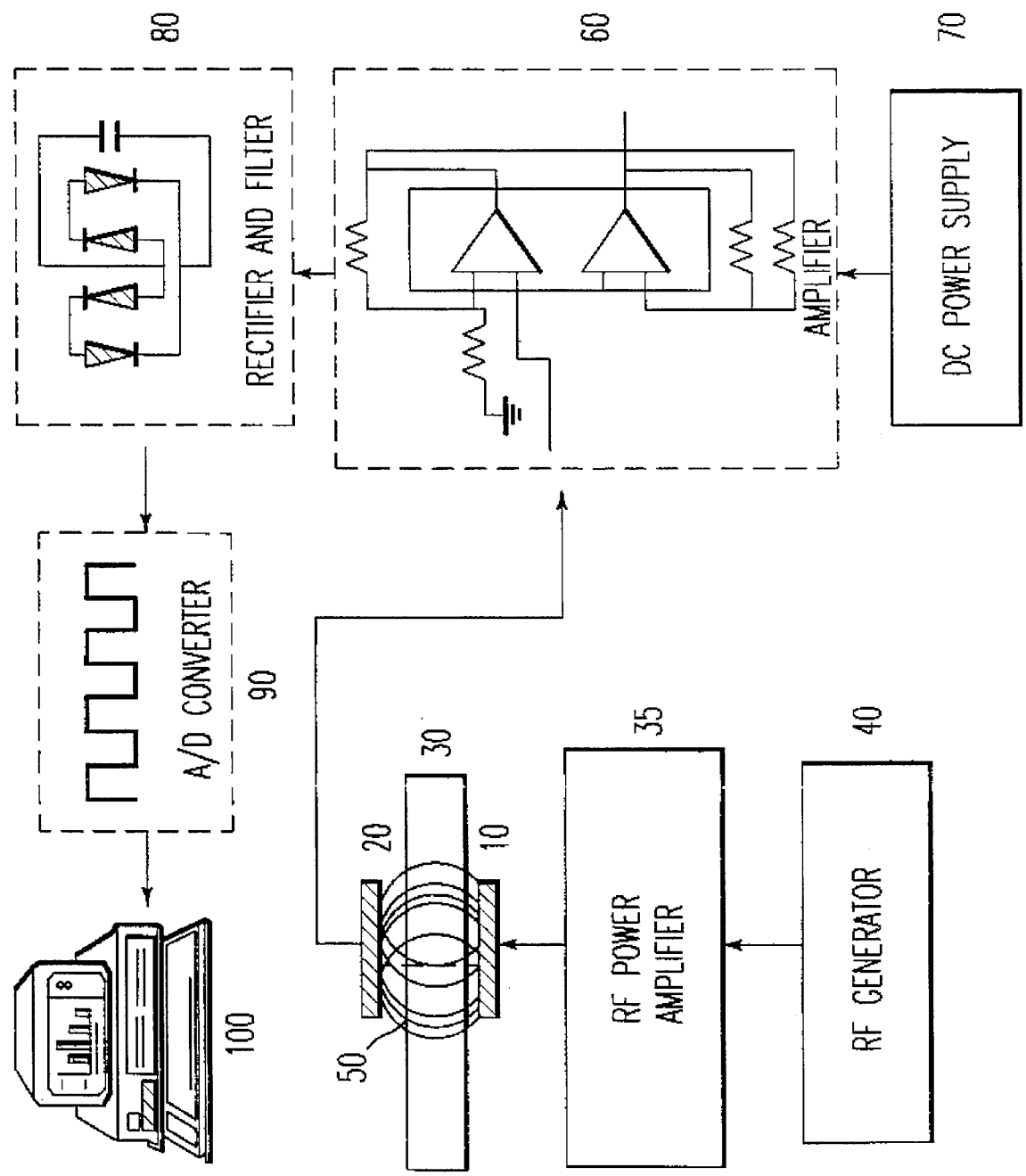
FIG. 2 illustrates schematically an apparatus to generate and detect dielectric response values between a pair of electrodes for clear wood, knot areas, and voids in a piece of lumber or veneer and transmit those signals to a computer.

The capacitance bridge in FIG. 1, consisting of capacitor electrodes 10,20 and generator 40, is connected to an amplifier 60 as shown in FIG. 2. Power is supplied to the amplifier 60 by a power supply 70. The amplifier provides a gain of 40 to 60 db to the input signal from the upper capacitor electrode 20 of the capacitance bridge. The amplified signal passes through a bridge rectifier and a filter 80. The rectified and filtered signal is converted from an analog to digital signal by an analog to digital convertor 90 and the digital signal is fed to a computer 100.

Figure 3:
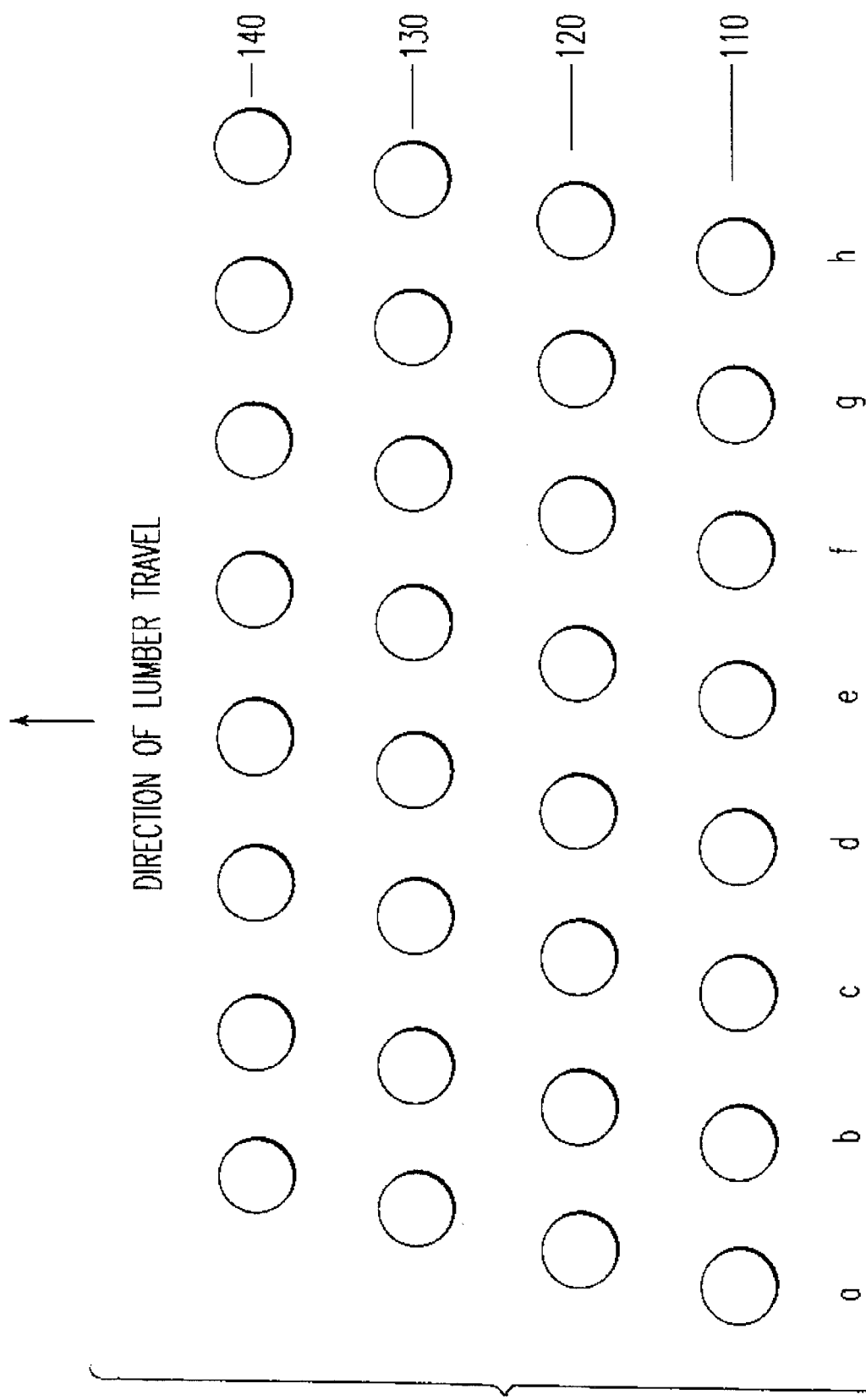
FIG. 3 schematically illustrates the top view of an array of 32 pairs of electrodes arranged in four rows extending substantially perpendicular to the path of travel of a piece of lumber or veneer. An identical array of 32 electrodes will be located opposite those indicated in FIG. 3. The lumber or veneer passes between these two arrays. Therefore, each of the 32 electrodes has an identical electrode opposite to it as shown in FIG. 1. The piece of lumber or veneer passes between the two arrays of opposite electrodes in the direction indicated in FIG. 3.

FIGS. 1 and 2 each illustrate the workings of a single opposed pair of capacitor electrodes. FIG. 3 shows a scanning head developed for scanning lumber composed of a top view of 32 capacitors. The narrow width of the FIG. 3 example of a 32 capacitor head is limited to scanning lumber parts an unrealistically maximum width of about 6 inches. This is because a few electrodes along each edge must scan only air to allow accurate lumber edge determination. For this purpose, lumber width must be approximately centered in the scanner head. The capacitor head is comprised of 4 slightly diagonal rows 110, 120, 130, and 140 of 8 capacitors a, b, c, d, e, f, g, h each. A 1-inch space is allowed between the centers of each adjacent capacitor electrode 110a, b, c, d, e, f, g, h to prevent electrical field cross talk between electrodes in the same plane. In this example the space allowed between edges of adjacent capacitor electrodes 110a, b, c, d, e, f, g, h is ½ inch. The capacitor electrodes a–h are round as illustrated in FIG. 3. The distance between the capacitors in a row of adjacent capacitors 110a, b, c, d, e, f, g, h may be varied as desired. The capacitor electrodes may also be of any desired shape and size so long as the knots and voids are detected with the desired degree of accuracy.

Rows subsequent to the first row 110a, b, c, d, e, f, g, h are not required, but scanning resolution is improved with additional rows of capacitors that overlap and scan the unscanned space between the capacitors of the initial row. In this example, a second row of capacitors 120a, b, c, d, e, f, g, h is placed so as to scan ¼ inch of the unscanned ½ inch of wood between the previous adjacent capacitors 110a, b, c, d, e, f, g, h in the first row. Likewise a third row of capacitors 130a, b, c, d, e, f, g, h scans the remaining ¼ inch between the adjacent first row capacitors 110a, b, c, d, e, f, g, h. The fourth row of capacitors 140a, b, c, d, e, f, g, h provides the same overlapping of the third row of capacitors 130a, b, c, d, e, f, g, h that the third row 130a, b, c, d, e, f, g, h provides for the second row 120a, b, c, d, e, f, g, h and that the second row provides for the first row. The capacitor scanner head shown in FIG. 3, therefore, has 32 capacitors that scan across the lumber width at ¼ inch intervals as the lumber passes between the pairs of capacitor electrodes.

The number of capacitors per row may be increased or decreased to correspond to the width of the material being scanned. Likewise, additional rows of capacitors may be added to increase the depth of the scanner head to improve resolution. The capacitor overlap, which is 50 percent in the configuration described in FIG. 3 may be more or less than this amount.

The numerical values obtained from converting analog to digital signals from the capacitors are stored in a computer 100 in a two-dimensional array that describes the across-thickness dielectric properties of the lumber.

The previously-referred-to recalibration function employed for each piece of lumber results from the array method employed to process the received lumber dielectric response values. By this array method all data for each piece of lumber is collected prior to processing. The array size is determined by lumber length and the width of the capacitors employed to scan the lumber. For example, the capacitor scanner head represented by FIG. 3 will have 32 voltage values representing the array width with a distance of ¼-inch separating each of the 32 voltage values. The leading and starting edge of each board may be defined prior to obtaining scanned values. This may be done by employing a photocell(s) to detect board ends. Alternately, the scanner may continuously sample values with a decrease in dielectric response serving to indicate the trailing end of a leading board; a subsequent increase would indicate the starting edge of a board. By either method, a 1 to 2 inch gap between consecutive boards on the conveyor is required.

Assume that the time interval for frequency of voltage samples obtained along the lumber width is at a uniform speed that allows a ¼-inch distance between each series of sampled values from the 32 capacitors. In this case, an 8-foot long piece of lumber up to 6 inches wide will be described by a 32 (wide) by 384 (long) element array, with each element ¼-inch distance from adjacent elements.

The 32 by 384-element board array can then be searched to determine lumber width and presence of defects. This array may alternately be defined as comprised of 32 columns with each column containing 384 digital values. Areas outside the lumber width and those that represent included voids in the wood will be indicated by very low voltage values representing the dielectric response of air. Clear wood will be indicated by higher voltage values than voids, and knots will be indicated by higher voltage values than clear wood. For southern yellow pine lumber of 1½ inch thickness, with capacitor electrodes spaced 0.125-inch from the wood surface there will be approximately a 0.5 volt difference between clear and knot wood. This difference in voltage diminishes by about 0.1 volt (i.e., to 0.4 volt) as head spacing is increased to 0.250-inch distance from wood surface.

Figure 4:
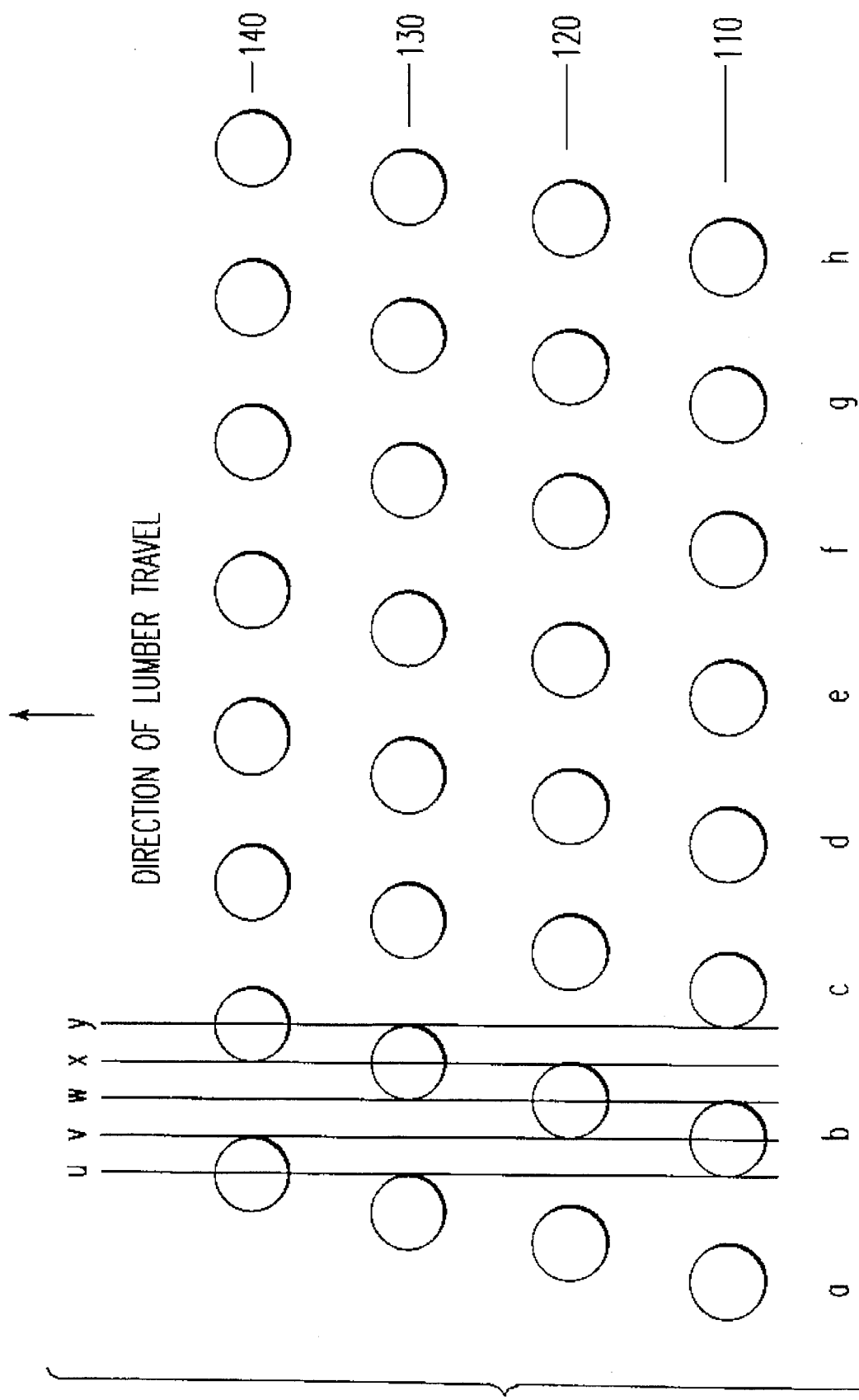
FIG. 4 is a schematic illustration similar to FIG. 3, further illustrating lines corresponding to potential positioning of board edges with respect to the array of electrodes, as the board passes in the direction indicated.

The difference in voltage values between air, knots, and clear wood allows the array to be searched to determine board edge, knot and included void locations. Recall, that in this example, board ends are detected by a photocell. By the array method, lumber edges are located prior to locating knots and voids. The lumber edges as approached from a direction exterior to the lumber are indicated by a sudden rise in dielectric response value above the dielectric response of air. When dielectric response values initially rise, indicating the lumber edge, one or two column of voltage values (i.e., along the out edges of the lumber) must be disregarded for the next described computation of the mean value of clear wood. This is because dielectric response values for these two columns are somewhat lower than would be expected for clear wood. These low values result due to the scanned object's edge passing only partially over a capacitor or capacitors. For example, if the board edge fell along line u in FIG. 4, it would cover only one-half of capacitor a in row 140 and would completely miss all other capacitors. In this case one column of the computer array would have a dielectric value equal to approximately one-half that of the array columns that are completely covered by wood. For this reason this column of low values should not be included when computing the mean value of clear wood. Similarly, dielectric values will also be equally low for board edges falling along lines v, w, x, y, and any similarly positioned lines located in the remainder of the array. For the more general case of board edges falling between lines u and v, v and w, w and x, and x and y, as well as for lines similarly positioned, only a portion of the surface area of each of two electrodes will be covered by wood. In this situation, the array values represented by the data obtained by these electrodes will be lower than for electrodes covered completely by wood. Therefore, for this situation the two columns of array values representing the board edge should not be included in the computation of the mean value of clear wood.

Following the exclusion from the array of the low values at board edges, an algorithm is employed to determine the mean and variance of voltage values received across the wood thickness. This algorithm assumes that clear wood will represent a specified percentage of the total surface area of the wood surface. Statistical Z table values are then used to include the specified percentage of clear wood in the computation of a mean dielectric value for clear wood. For example, to include 80 percent of population values in a clear wood voltage value computation we include all values that are ±1.282 times the computed standard deviation value. The resulting value gives the distance from the mean required to insure that 10 percent of the values are included in each tail of a bell-shaped normal distribution. Therefore, 10 percent of the values will be below the lower cut-off value and will be defined as voids, likewise, 10 percent of the values will be above the upper cut-off value and will be defined as knots.

The percentage of clear wood estimated to be contained in each group of scanned lumber may be entered by the user based on the approximate lowest percentage of clear wood to be found in any individual piece of lumber in the group. A group of pieces of lumber containing many knots would require a lower estimate of clear wood percentage than a group of pieces of lumber containing fewer knots. Incorrectly specifying this percentage estimate may result in a loss of resolution.

The lumber array can then be searched for values above or below the threshold value computed to represent clear wood. For this computation, the two columns of values excluded on each lumber edge prior to computing the mean and standard deviation are added back to the array when the array is searched for knots. Knots will have values much higher than clear wood and voids will have values much lower than clear wood. The edge values will generally be only slightly lower than those for the clear wood. This allows both knots and voids to be detected in these edge rows, if present.

The algorithm described here is one of many that could have been employed to allow differentiation of knots and voids from clear wood. The description was for illustrative purposes only and is not meant to restrict the array processing method to this single algorithm. Any algorithm that could be employed to allow differentiation of knots and voids in the array data fall within the scope of this invention.

The recalibration function supplied by the array method is obtained because no predetermined voltage values for clear wood, knots, or voids are assumed. The discrimination between clear wood, knots, and voids are made entirely by comparing values within the array of dielectric response values collected for each board.

The array method currently relies on the processing of the entire array of values for wood type determination. However, processing a reduced portion of the array may be required to reduce computation time. This may be especially desirable for long lumber. Therefore, our method does not preclude processing array segments rather than the entire array.

In its current configuration, pieces of lumber are conveyed along a substantially linear path of travel and pass between the upper and lower electrodes of 4 capacitor rows 110, 120, 130, 140 in FIG. 3 such that these rows 110, 120, 130, 140 are perpendicular to the long axis of the lumber. It will generally be necessary to increase the array width to slightly over 4 feet for scanning veneer, as sheets of 4-foot width are standard. It is also possible to increase the length of the rows further such that lumber or veneer may be passed transversely across the rows 110, 120, 130, 140, such that lumber or veneer long axis is parallel to the rows 110, 120, 130, 140. This transverse feeding of the lumber between capacitors would require increasing capacitor numbers to a magnitude adequate for desired resolution. For example, to scan a 16-foot-long piece of lumber would require 194 capacitors in each row when the piece of lumber is passed transversely with the long axis parallel to the rows 110, 120, 130, 140 to provide the same resolution as the FIG. 3 configuration in which lumber is passed perpendicular to the rows 110, 120, 130, 140.

The present invention was developed to scan for knots and voids in wood that has been reduced to uniform thickness. When wood is scanned that departs significantly from a uniform thickness it may be necessary to measure wood thickness during scanning and to adjust the dielectric values sampled through the wood above or below a mean thickness. Several devices for measuring wood thickness are available commercially.

A threshold-value method was adopted for the development of the defect detection and delineation algorithms. This method considers the scanned wood shape to be made up of a two-dimensional array of tiles. The sides of the tiles equal the intervals at which dielectric measurements have been taken on the wood, which was ¼ inch in the example described by FIG. 3. The position of a tile on the wood is defined by a (X, Y) value. Each of the tiles contains the dielectric response value measured at the center of its corresponding position. Two threshold values are computed, one for knot identification and one for void identification. All tiles which have dielectric values above the knot threshold value are identified as knots; those below the void threshold value are identified as voids. This method considers a knot or void within a piece of lumber to be an area of contiguous defective tiles. The algorithm searches for such areas of defective tiles. Once an area of defective tiles is found, it is delineated within a rectangle. The coordinates (Xmin, Ymin), (Xmax, Ymax) of this rectangle are determined using the following steps:

1. The first defective (knot or void) tile found in an area of defective tiles is located. The two-dimensional array consisting of the dielectric values is searched to locate the first defective tile. This search is made in the direction (X or Y) in which the board is scanned.

2. The coordinates of the rectangle are initialized to the (X,Y) position of the initial tile as follows:

Xmin=Xmin=X

Ymax=Ymax=Y

3. A single tile has 8 contiguous tiles surrounding it. These tiles are examined to determine if any are defective.

4. All defective tiles among the 8 tiles surrounding the located defective tile are added to a list of defective tiles.

5. Each tile among the newly added contiguous defective tiles is, in turn, examined for defective contiguous neighbors. If these neighboring tiles are defective they are also added to the list. After a tile is examined for defective contiguous tiles, it is removed from the search list.

6. The (X,Y) position of each defective tile added to the list is compared with the present coordinates of the rectangle. If necessary, the present coordinates are reset in the following manner:
   If X<Xmin, Xmin=X
   If X>Xmax, Xmax=X
   If Y<Ymin, Ymin=Y
   If Y>Ymax, Ymax=Y 7. The values of the minimum and maximum X- and Y-coordinates after the comparison of the last selected defective tile are taken as the coordinates of the rectangle which inscribes the defect.

In some cases knot and/or void defects may be very close to each other. In such cases the rectangles inscribing these areas of defective tiles may overlap or be juxtaposed within fractions of an inch of each other. In this situation, a merging function may be invoked to merge overlapping or closely adjacent knots or voids. This acts to reduce the computer solution time needed to process data in any subsequently applied lumber processing simulations. The definition of the distance between closely adjacent rectangles that would cause them to be merged is a user-defined variable.

Merger of rectangles proceeds by comparing the coordinates of two rectangles that lie overlapped. Rectangles that lie close to each other are also considered for merger. The lower of the two lower coordinates and the higher of the two higher coordinates of the overlapping or close rectangles, are taken as the coordinates of the rectangle resulting from the merger. Merger of the rectangles is continued in this fashion until all overlapped or close rectangles are merged.

The described algorithms for detecting and delineating knot and void defects with rectangles are examples of many that could be employed for this purpose. Any algorithm that performs these knot and void detection and delineation functions in the context of the dielectric scanning of wood falls within the scope of this invention.

(2) Estimation of Wood Strength

In the configuration of the present invention required to estimate lumber strength, the array method is employed exactly as described above to determine the size and location of knots and voids. This provides the information on the influence of knot size and location on the strength of wood. The determination of clear wood strength is obtained by comparing the dielectric values representing clear wood to base values previously determined for wood of known density. The wood moisture content of the base value must be known and the moisture content of the scanned material must be determined by scanning the wood with an in-line moisture meter. A correction algorithm to adjust the dielectric values for a moisture content different than that of the base value must be employed. The dielectric response value adjusted for moisture content will allow estimation of clear wood density and from this density, clear wood strength can be estimated. The strength of the piece of lumber is then estimated from the combined information on estimated clear wood strength and the influence of knot and void size and location.

An example of a suitable algorithm for use in estimating wood strength is as set forth below. The relationship between moisture content and voltage attenuation in the range of moisture content between 6 to 25 percent is linear. The example assumes that the relationship between voltage and wood density is also linear.

EQUATION

The following two equations can be used in conjunction with the disclosed method and apparatus to estimate the strength of wood when moisture content (MC) and density vary from the moisture content and density of the base wood sample.

SV=Sensed voltage

SVAMC=Sensed voltage adjusted for MC different from base moisture content

BV=Base voltage at base MC

BS=Base strength of wood at base MC and density

ES=Estimated strength of wood $$SVAMC \cdot \left(1.0 \cdot \frac{(BV \cdot SV)}{BV}\right) \cdot SV$$

$$ES \cdot \left(1.0 \cdot \frac{(SVAMC \; BV)}{BV}\right) \cdot BS \cdot \left(\frac{(SVAMC \; BV)}{BV}\right) \cdot BS$$

The first equation is used to adjust the sensed voltage for the variation in moisture content and the second equation is used to estimate the strength of wood. The moisture content of wood is measured independently by a commercially available in-line moisture meter. If the moisture content is equal to the base moisture content then the first equation will not be used to adjust sensed voltage. In that case, only the second equation is required to estimate the wood strength. Assuming BS=70,000 kPa BV=2.5 Volts SV=2.6 Volts at 15% MC and base moisture content is 15%.

Since the moisture content is the same, only the second equation is required to estimate the strength of wood.

$$ES \cdot \left(1.0 \cdot \frac{2.6 \cdot 2.5}{2.5}\right) \cdot 70{,}000 \cdot \left(1.0 \cdot \frac{0.1}{2.5}\right) \cdot 70{,}000 \cdot 72{,}800 \text{ kPa}$$

If moisture content changes to 20%, for example, and the sensed voltage is still 2.6 volts then the first equation is applied to adjust the sensed voltage.

$$SVAMC \cdot \left(1 \cdot \frac{12.5 \; 2.6}{2.5}\right) \cdot 2.6 \cdot 2.496 \text{ volts}$$

$$ES \cdot \left(1 \cdot \frac{2.496 \; 2.5}{2.5}\right) \cdot 70{,}000 \cdot 69{,}888 \text{ kPa}$$

EXPERIMENTAL RESULTS

Experiments performed with the present invention have shown it accurate in detecting knots and voids, both hidden and exposed, in wood. Detailed experiments testing the accuracy of the present invention to detect knots in southern yellow pine (SYP) dimension lumber of 1½-inch thickness, were performed. The device tested was the Model 2 DHM. Model 2 employs 32 capacitors as shown in FIG. 3 with each capacitor composed of 2 opposed parallel capacitor electrodes. Capacitor electrodes were round and ½ inch in diameter with a surface area of 0.196 inches.

The oscillator frequency of the Model 2 DHM is 200 kHz, and it has a voltage output of 28.28 volts RMS. A Wavetek oscillator Model #2520A, EIN RF power amplifier Model #411LA, Topward D.C. power supply Model #TPS4000, and PC's Limited 486DX computer Model #PC110 were used in the experiments.

Ten SYP 2×4's were randomly selected at a local lumber yard. Four-foot long specimens were cut from the 2/4's. Each specimen contained one knot of approximately 1-inch diameter on one surface. Knots were selected that passed through board thickness and also showed on the opposite face.

The knot surface shapes on opposite faces were projected into a single plane to simulate the knot shape as the opposing heads of the DHM would sense it across the lumber thickness. A grid system was sketched on the board surface allowing for the combined projected dimensions to be determined.

Selected from the ten available, five specimens were randomly selected to perform a calibration step for threshold value determination. Each of the 5 specimens was passed lengthwise between the DHM heads by a single-axis positioning table at a speed of 2.5 inch per second. Each specimen was passed between the DHM heads 5 times to determine DHM repeatability. The knot length and width as measured were then compared with the mean DHM-sensed length and width. Statistical tests comparing the actual mean knot length and width to the DHM-sensed mean knot length and width were performed. The results showed that there was no significant difference in actual and sensed mean knot dimensions for repeated passes of the same specimen through the capacitors.

Tests to determine the repeatability of a sampled dielectric response over time at a single point on the sample lumber were also performed. A single capacitor was positioned with clear wood between the electrodes and 10 dielectric response values were sampled at that spot at one-second intervals. Five sample pieces of lumber had this test performed. Statistical tests showed no significant difference between the values sampled at one spot over the 10 second time interval.

Tests were also conducted that showed the DHM effective in detecting hidden and spike knots in lumber.

Obviously, additional modifications and variations of the present invention are possible in light of the above findings. It is therefore to be understood that within the scope of the appended claims, the invention may be practiced otherwise than as specifically described herein.

What is claimed as new and desired to be secured by letters patent of the United States is:

1. A method for determining the presence and location of knots in a piece of lumber or veneer, comprising the steps of:
   (a) providing pairs of opposed capacitor electrodes with a first electrode of each pair located on one side of a path of travel of the wide face of the piece of lumber or veneer and with a second electrode of each pair located on the other side of said path of travel of the wide face of the piece of lumber or veneer with said opposed capacitor electrodes arranged to be adjacent to but slightly spaced from the piece of lumber or veneer as the piece of lumber or veneer is conveyed past said opposed capacitor electrodes;
   (b) applying an alternating voltage in the radio frequency range to the second electrode of each pair of opposed capacitor electrodes;
   (c) detecting the peak voltage signals transmitted through said piece of lumber or veneer at the first electrode of each pair of opposed capacitor electrodes;
   (d) repeating step (c) a plurality of times as the piece of lumber passes said opposed capacitor electrodes to thereby form a two-dimensional array of sensed peak voltage signals with each peak voltage signal corresponding to a unique location on the piece of lumber or veneer;
   (e) designating an upper threshold voltage value above a mean and below a highest peak voltage signal of a voltage variance with any suitable algorithm; and
   (f) searching said array of voltage values for voltage values above said upper threshold value and designating the voltage values thus found as corresponding to knots in the piece of lumber or veneer.

2. The method of claim 1 including the steps of:
   (a) designating a lower threshold value below the mean and above a lowest peak voltage signal of said voltage variance; and (b) searching the array of voltage values for voltage values below a lower threshold value and designating the voltage values thus found as corresponding to voids in the piece of lumber.

3. The method according to claim 1 including providing a plurality of said pairs of opposed capacitor electrodes in a row extending perpendicular to the path of travel of said piece of lumber or veneer with the space between adjacent pairs of opposed capacitor electrodes in the row being substantially equal.

4. The method according to claim 3 including providing a plurality of said rows of said pairs of opposed capacitor electrodes with spacing of the pairs of opposed capacitor electrodes in each row being substantially equal and with the pairs of opposed capacitor electrodes in each row being laterally offset with respect to the pairs of opposed capacitor electrodes in an adjacent row.

5. The method according to claim 4 wherein each pair of electrodes is arranged in a column and the step of computing the mean and voltage variance comprises omitting the voltage values for any said column of opposed capacitor electrodes which has one or more capacitors that are partially or completely outside of either longitudinal edge of the piece of lumber or veneer as the piece of lumber or veneer is conveyed past said opposed capacitor electrodes.

6. The method according to claim 5 wherein the voltage values of those opposed capacitor electrodes which are located partially outside of either longitudinal edge of the piece of lumber or veneer are included in the array when searching said array of voltage values for voltage values above said upper threshold value and designating the voltage values thus found as corresponding to knots in the piece of lumber or veneer.

7. The method according to claim 6 further comprising the steps of:

(a) designating a lower threshold value below the mean and above the lowest peak voltage signal of said voltage variance;

(b) adding the voltage values for the opposed capacitor electrodes which extend partially beyond either longitudinal edge of the piece of lumber or veneer to the array; and (c) searching said array of voltage values for voltage values below the lower threshold value and designating the voltage values thus found as corresponding to voids in the piece of lumber or veneer.

8. The method according to claim 1 including the step of measuring the thickness of the piece of lumber and adjusting the peak voltage signal of each electrode based on the thickness of the lumber at the location of the respective sensing electrode to correspond to the voltage value that that piece of lumber would have at the same location if the piece of lumber had a given uniform thickness.

9. A method for determining the presence and location of knots and voids in a piece of lumber or veneer, comprising the steps of:

(a) conveying a piece of lumber or veneer along a substantially linear path of travel;

(b) providing pairs of opposed capacitor electrodes with a first electrode of each pair located on one side of said path of travel of the piece of lumber or veneer and with a second electrode of each pair located on the other side of said path of travel of the under face of the piece of lumber or veneer, said opposed capacitor electrodes arranged to be adjacent to but slightly spaced from the wide face of the piece of lumber or veneer as the piece of lumber or veneer is conveyed past said opposed capacitor electrodes and said pairs of opposed capacitor electrodes further arranged in a row perpendicular to the path of travel of the piece of lumber or veneer with the space in between adjacent pairs of electrodes being substantially equal;

(c) applying an alternating voltage in the radio frequency range to the second electrode of each pair of opposed capacitor electrodes;

(d) detecting the peak voltage signals transmitted through said piece of lumber at the first electrodes of each pair of opposed capacitor electrodes;

(e) repeating step (d) a plurality of times as the piece of lumber passes said opposed capacitor electrode to thereby form a two dimensional array of sensed peak voltage signals with each peak voltage signal corresponding to a unique location on the piece of lumber;

(f) designating an upper threshold voltage value above a mean and below a highest peak voltage signal of a voltage variance by any appropriate algorithm;

(g) designating a lower threshold value below the mean and above a lowest peak voltage signal of said voltage variance by any appropriate algorithm;

(h) searching said array of voltage values for voltage values above said upper threshold value and designating the voltage values thus found as corresponding to knots in the piece of lumber or veneer;

(i) searching the array of voltage values for voltage values below the lower threshold value and designating the voltage values thus found as corresponding to voids in the piece of lumber or veneer;

(j) dividing said array into tiles and assigning each tile a specific X, Y, coordinate system value;

(k) using any appropriate algorithm for searching the two dimensional array for peak voltage values above the upper threshold value and for peak voltage values below the lower threshold value including locating a voltage signal value above the upper threshold value or below the lower threshold value thereby defining each such element as representing an area of knot or void; and (l) using any appropriate algorithm for a knot or void area in enclosing the areas defined by the defective tile in a rectangle.

10. The method according to claim 9 including the step of merging any overlapping rectangles by any appropriate algorithm.

11. The method according to claim 10 including the step of merging rectangles that do not overlap but lie within a user selected distance to each other by any appropriate algorithm.

12. The method according to claim 9 further comprising estimating the strength of the piece of lumber by performing the following additional steps:

(a) classifying the wood that has voltage values between the upper threshold level and the lower threshold level as clear wood;

(b) comparing the voltage values of the clear wood to base values previously determined for wood of known density;

(c) determining the moisture content of the piece of lumber being scanned;

(d) comparing the moisture content of the scanned piece of lumber to the moisture content for the previously determined piece of lumber of known density;

(e) adjusting the voltage values for the scanned piece of lumber based on the difference in moisture content of the scanned piece of lumber to the piece of lumber of known density; and (f) estimating the strength of the piece of lumber based on the adjusted voltage values and the information concerning the size and location of defective areas attributed to knots and voids in the scanned piece of lumber and for which the corresponding voltage values in the two dimensional array have been inscribed in rectangles.

* * * * *